(12) United States Patent
Whitehurst et al.

(10) Patent No.: US 9,352,145 B2
(45) Date of Patent: May 31, 2016

(54) METHODS AND SYSTEMS FOR TREATING A PSYCHOTIC DISORDER

(75) Inventors: Todd K. Whitehurst, Santa Clarita, CA (US); Kristen N. Jaax, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1490 days.

(21) Appl. No.: 12/497,386

(22) Filed: Jul. 2, 2009

(65) Prior Publication Data

US 2009/0270944 A1    Oct. 29, 2009

Related U.S. Application Data

(62) Division of application No. 11/317,466, filed on Dec. 22, 2005, now abandoned.

(60) Provisional application No. 60/638,950, filed on Dec. 22, 2004.

(51) Int. Cl.
*A61N 1/36* (2006.01)
*A61N 1/05* (2006.01)
*A61N 1/372* (2006.01)
*A61N 1/375* (2006.01)

(52) U.S. Cl.
CPC ............ *A61N 1/0531* (2013.01); *A61N 1/0534* (2013.01); *A61N 1/36082* (2013.01); *A61N 1/3756* (2013.01); *A61N 1/37205* (2013.01)

(58) Field of Classification Search
USPC ............ 600/544, 545; 607/2, 45, 48, 59, 115, 607/116, 139
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |

(Continued)

FOREIGN PATENT DOCUMENTS

| | | |
|---|---|---|
| WO | WO 01/82398 A1 | 11/2001 |
| WO | WO 02/072194 A2 | 9/2002 |
| WO | WO 03/005465 A1 | 1/2003 |

OTHER PUBLICATIONS

Zaksanis, K.K. et al., Searching the schizophrenic brain for temporal lobe deficits: a systematic review and meta-analysis; Psyco Med 2000; 30:491-504.

(Continued)

*Primary Examiner* — Carl H Layno
*Assistant Examiner* — Jennifer Ghand
(74) *Attorney, Agent, or Firm* — Faegre Baker Daniels LLP

(57) ABSTRACT

Methods of treating a psychotic disorder include applying at least one stimulus to a stimulation site within a patient with an implanted stimulator in accordance with one or more stimulation parameters configured to treat the psychotic disorder. Systems for treating a psychotic disorder include a stimulator configured to apply at least one stimulus to a stimulation site within a patient in accordance with one or more stimulation parameters configured to treat the psychotic disorder.

12 Claims, 11 Drawing Sheets

(56) References Cited

U.S. PATENT DOCUMENTS

| | | | |
|---|---|---|---|
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,487,603 A | 12/1984 | Harris | |
| 4,562,751 A | 1/1986 | Nason et al. | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,092,835 A | 3/1992 | Schurig et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,299,569 A | 4/1994 | Wernicke et al. | |
| 5,312,439 A | 5/1994 | Loeb | |
| 5,501,703 A | 3/1996 | Holsheimer et al. | |
| 5,540,734 A | 7/1996 | Zabara | |
| 5,728,396 A | 3/1998 | Peery et al. | |
| 5,938,688 A | 8/1999 | Schiff | |
| 5,975,085 A | 11/1999 | Rise | |
| 6,016,449 A | 1/2000 | Fischell et al. | |
| 6,051,017 A | 4/2000 | Loeb et al. | |
| 6,164,284 A | 12/2000 | Schulman et al. | |
| 6,167,311 A | 12/2000 | Rezai | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,280,873 B1 | 8/2001 | Tsukamoto | |
| 6,308,101 B1 | 10/2001 | Faltys et al. | |
| 6,368,315 B1 | 4/2002 | Gillis et al. | |
| 6,381,496 B1 | 4/2002 | Meadows et al. | |
| 6,418,344 B1 | 7/2002 | Rezai et al. | |
| 6,458,171 B1 | 10/2002 | Tsukamoto | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,620,151 B2 | 9/2003 | Blischak et al. | |
| 6,666,845 B2 | 12/2003 | Hooper et al. | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 2001/0046625 A1 | 11/2001 | Ruth et al. | |
| 2001/0053476 A1 | 12/2001 | Ruth et al. | |
| 2002/0013612 A1 | 1/2002 | Whitehurst | |
| 2002/0087201 A1 | 7/2002 | Firlik et al. | |
| 2002/0091419 A1 | 7/2002 | Firlik et al. | |
| 2002/0151939 A1 | 10/2002 | Rezai | |
| 2002/0188330 A1 | 12/2002 | Gielen et al. | |
| 2003/0171711 A1* | 9/2003 | Rohr et al. | 604/67 |
| 2004/0158119 A1 | 8/2004 | Osorio et al. | |
| 2004/0225335 A1* | 11/2004 | Whitehurst et al. | 607/45 |
| 2005/0048641 A1* | 3/2005 | Hildebrand et al. | 435/283.1 |
| 2005/0065574 A1* | 3/2005 | Rezai | 607/45 |
| 2006/0004422 A1 | 1/2006 | De Ridder | |
| 2006/0058856 A1* | 3/2006 | Morrell | 607/46 |
| 2006/0100671 A1 | 5/2006 | Ridder | |
| 2006/0178709 A1 | 8/2006 | Foster et al. | |
| 2007/0005115 A1* | 1/2007 | Lozano et al. | 607/45 |
| 2007/0167991 A1 | 7/2007 | DiLorenzo | |

OTHER PUBLICATIONS

Fletcher, P., et al., Abnormal cingulate modulation of fronto-temporal connectivity in schizophrenia, Neuroimage 1999, 9: 337-42.

Wantanabe, T., et al., Modification of behavioral responses induced by electrical stimulation of the ventral tegmental area in rats, Behavioral Brain Research, Jun. 1998, 93(1-2): 119-29.

Hoffman, R., et al., Transcranial magnetic stimulation of left temporoparietal cortex and medication-resistant auditory hallucinations, Arch. Gen. Psychiatry, Jan. 2003, 60(1):49-56.

Siegel, B., et al., Corticalstriatal-thalamic circuits and brain glucose metabolic activity in 70 unmedicated male schizophrenic patients, Am. J. Psychiatry, 1993, 150: 1325-36.

Hazlett, E., et al., Three-dimensional analysis with MRI and PET of the size, shape, and function of the thalamus in the schizophrenia spectrum, Am. J. Psychiatry, 1999, 156:1190-1199.

Danos, P. et al., The ventral lateral posterior nucleus of the thalamus in schizophrenia: a post-mortem study, Psychiatry Res. Feb. 15, 2002; 114(1):1-9.

Deicken, R. et al., Magnetic resonance imaging of the thalamus in male patients with schizophrenia, Schizophr Research Dec. 1, 2002; 58(2-3); 135-44.

Delisi, L. et al., Increased temporal lobe glucose use in chronic schizophrenic patients, Biol Psychiatry 1989; 25: 835-51.

Office Action dated Jul. 7, 2008 in U.S. Appl. No. 11/317,466, filed Dec. 22, 2005, inventor: Todd K. Whitehurst, (27 pages).

Office Action dated Dec. 17, 2008 in U.S. Appl. No. 11/317,466, filed Dec. 22, 2005, inventor: Todd K. Whitehurst, (11 pages).

Office Action dated Mar. 13, 2009 in U.S. Appl. No. 11/317,466, filed Dec. 22, 2005, inventor: Todd K. Whitehurst, (11 pages).

* cited by examiner

METHODS AND SYSTEMS FOR TREATING A PSYCHOTIC DISORDER

RELATED APPLICATIONS

This application is a divisional of co-pending U.S. application Ser. No. 11/317,466, filed on Dec. 22, 2005, which claims the priority under 35 U.S.C. §119(e) of previous U.S. provisional application Ser. No. 60/638,950, filed Dec. 22, 2004, which is incorporated herein by reference in its entirety.

BACKGROUND

Psychotic disorders distort a person's perception of reality. Schizophrenia is a particularly severe type of psychotic disorder and is characterized by persistent defects in a patient's perception or expression of reality. Approximately one percent of the population develops schizophrenia during their lifetime. More than two million Americans suffer from the illness in a given year.

A person experiencing untreated schizophrenia typically demonstrates grossly disorganized thinking and may also experience delusions or auditory hallucinations. Although the illness primarily affects cognition, it can also contribute to chronic problems with behavior or emotions.

There is no objective biological test for schizophrenia, though studies suggest that genetics and biochemistry are important contributing factors. Current research into the development of the disorder often focuses on the role of neurobiology, although an identifiable biological cause has not been found.

Hence, diagnosis of schizophrenia is based on the self-reported experiences of the patient, in combination with secondary signs observed by a psychiatrist or other competent clinician. The most commonly used criteria for diagnosing schizophrenia are from the American Psychiatric Association's Diagnostic and Statistical Manual of Mental Disorders (DSM) and the World Health Organization's International Statistical Classification of Diseases and Related Health Problems (ICD).

According to the DSM, to be diagnosed as having schizophrenia, a patient must display two or more of the following symptoms for a significant portion of time during a one-month period: delusions, hallucinations, disorganized speech (e.g., frequent derailment or incoherence, speaking in the abstract), grossly disorganized behavior (e.g., dressing inappropriately, crying frequently), or such negative symptoms as lack or decline in emotional response, lack or decline in speech, or lack or decline in motivation, where a negative symptom is defined as a decline in, or lack of, a, normal behavior. In addition, the patient must show significant social and/or occupational dysfunction as a result of these symptoms.

Many hypotheses have been formulated as to the cause of schizophrenia. For example, infections (e.g., a slow virus), genetic disorders, autoimmune or immune dysfunctions, and environmental factors have all been advanced as possible causes of schizophrenia. The effectiveness of the neuroleptic drugs, which block dopamine as a transmitter, has led to the hypothesis that schizophrenia is the result of dysfunction of neurons utilizing dopamine as a neurotransmitter. In particular, some studies have hypothesized that there is an over activity in these neurons which utilize dopamine. However, recent studies have questioned the dopamine hypothesis because there is little evidence of elevated dopamine levels in many schizophrenic patients.

Other biochemical hypotheses have been put forward to explain the causes of schizophrenia. For example, newer medications that are a combination of dopamine receptor and serotonin receptor antagonists have been found to be equally or more effective than previously used dopamine antagonists, suggesting that excess serotonin may also play a role in schizophrenia.

Treatment options for patients suffering from schizophrenia and other psychotic disorders are limited. Although a cure for psychotic disorders does not currently exist, several antipsychotic drugs are available that may improve or stabilize symptoms for some patients. However, many of these drugs have undesirable side effects as they pass through the body to the brain after being taken orally or injected intravenously. Psychotherapy (e.g., cognitive behavioral therapy) or other forms of talk therapy may also be used to treat schizophrenia and other psychotic disorders. However, such psychotherapy usually only focuses on the direct reduction of the symptoms, such as issues of self-esteem, social functioning, and insight.

SUMMARY

Methods of treating a psychotic disorder include applying at least one stimulus to a stimulation site within a patient with an implanted stimulator in accordance with one or more stimulation parameters configured to treat the psychotic disorder.

Systems for treating a psychotic disorder include a stimulator configured to apply at least one stimulus to a stimulation site within a patient in accordance with one or more stimulation parameters configured to treat the psychotic disorder.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for treating a psychotic disorder are described herein. An implanted stimulator is configured to apply at least one stimulus to a stimulation site within a patient in accordance with one or more stimulation parameters. The stimulus is configured to treat the psychotic disorder and may include electrical stimulation, drug stimulation, gene infusion, chemical stimulation, thermal stimulation, electromagnetic stimulation, mechanical stimulation, and/or any other suitable stimulation. As used herein and in the appended claims, "treating" a psychotic disorder refers to any amelioration of one or more causes and/or one or more symptoms of the psychotic disorder.

Schizophrenia is one of the most common psychotic disorders that may be treated with the methods and systems described herein. However, it will be recognized that any other psychotic disorder (e.g., delusional disorders and schizoaffective disorders) may additionally or alternatively be treated with the methods and systems described herein. Patients suffering from delusional disorders experience one or more delusions in the absence of any other significant signs or symptoms of mental illness. Patients suffering from schizoaffective disorders experience both the symptoms of schizophrenia and one or more mood disorders (e.g., depression and bipolar disorders). Hence, as used herein, and in the appended claims, the term "psychotic disorder" will be used to refer to schizophrenia, a delusional disorder, a schizoaffective disorder, and/or any other psychotic or mood disorder.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
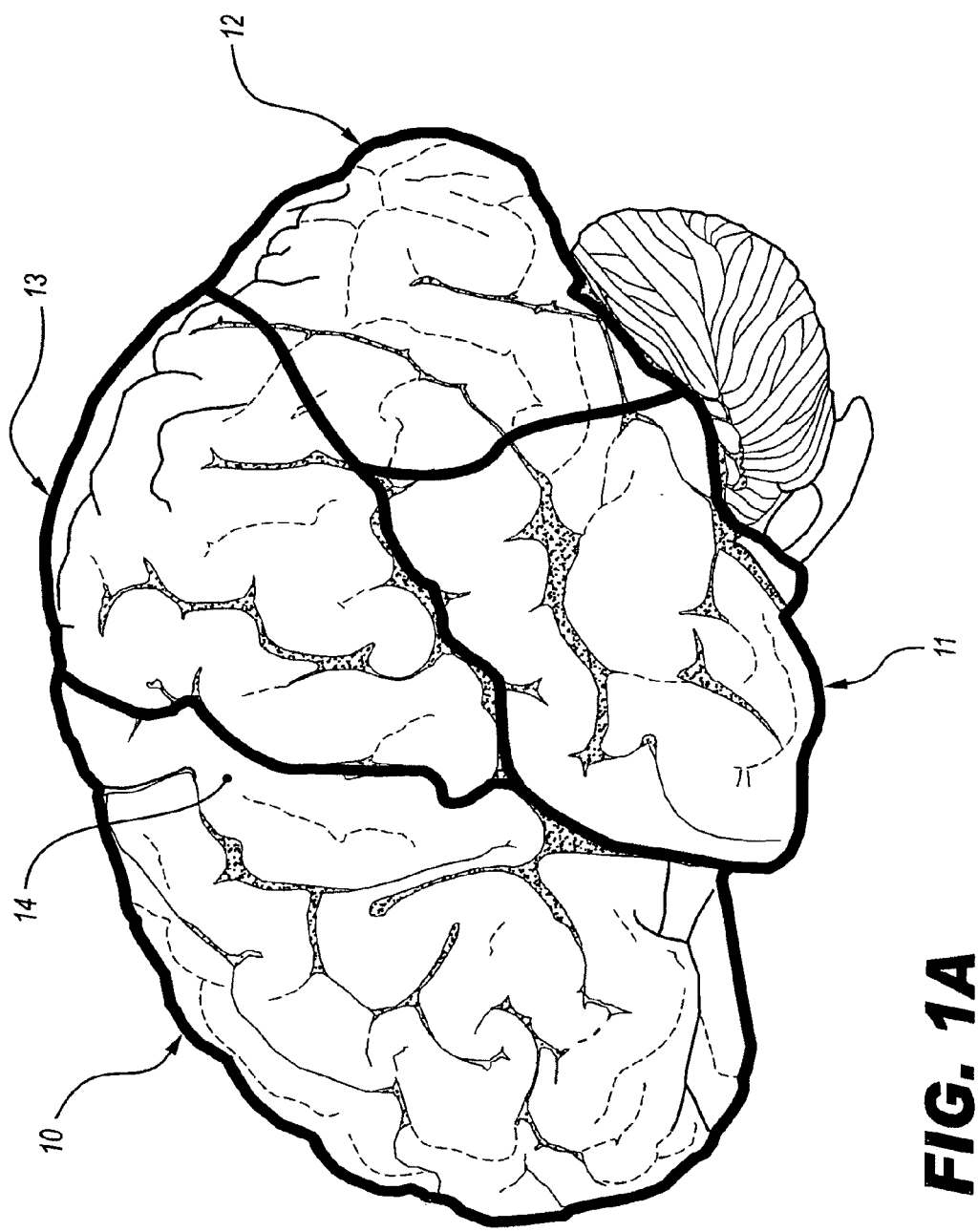
FIG. 1A depicts the lateral surface of the brain.

FIG. 1A depicts the lateral surface of the brain. As shown in FIG. 1A, the brain may be divided into a number of geographical lobes. The frontal lobe (10) is located at the front or anterior portion of the brain, the temporal lobes (11) are located on the sides or lateral portions of the brain, the occipital lobe (12) is located at the back or posterior portion of the brain, and the parietal lobe (13) is located at the top or superior portion of the brain toward the posterior of the brain. Each lobe contains areas responsible for a number of different functions.

The cerebral cortex (14) is the outermost layer of the brain and is involved in many complex brain functions including, but not limited to, memory, attention, perceptual awareness, thinking, language, and consciousness. The surface layer of the cerebral cortex (14) is called the neocortex. The neocortex is the most highly developed portion of the human brain and is believed to be involved with higher mental processes including, for example, planning, reasoning, and problem solving. It is also believed that the neocortex is linked to self-awareness and consciousness.

Figure 1B:
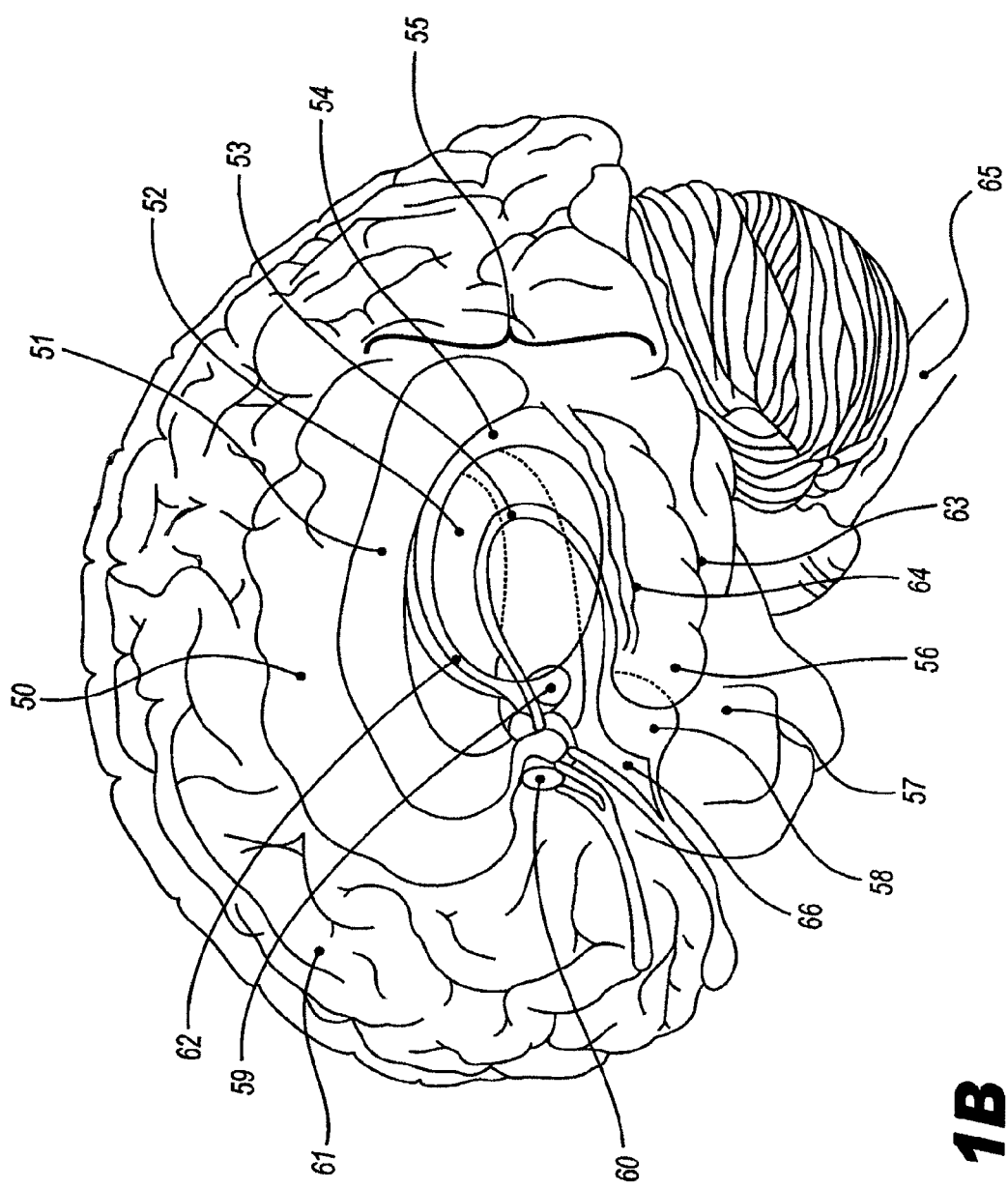
FIG. 1B is a perspective lateral view of the brain.

FIG. 1B depicts, in perspective lateral view, various structures within the brain. For example, FIG. 1B shows the thalamus (52), which processes information from the senses and relays such information to other parts of the brain. FIG. 1B also shows a number of structures that make up the limbic system. The limbic system includes, but is not limited to, the following subcortical structures: the cingulate gyrus (50), corpus collosum (51), stria terminalis (53), caudate nucleus (54), basal ganglia (55), hippocampus (56), entorhinal cortex (57), amygdala (58), mammillary body (59), medial septal nucleus (60), prefrontal cortex (61), and fornix (62). These structures are involved with emotion, learning, and memory.

FIG. 1B also shows the substantia nigra (63), ventral tegmentum (64), locus ceruleus (65), and nucleus accumbens (66). The substantia nigra (63) is located in the midbrain and is thought to be involved in certain aspects of movement and attention. It also contains neurons that produce the neurotransmitter dopamine. The ventral tegmentum (64) is also located in the midbrain and is believed to be involved in emotion, behavioral motivation, avoidance, and fear conditioning. The ventral tegmentum (64) contains many dopamine and serotonin neurons and is part of two major dopamine pathways: the mesolimbic pathway and the mesocortical pathway. The locus ceruleus (65) is a nucleus in the brain stem and is believed to be responsible for the physiological reactions involved in stress and panic. The nucleus accumbens (66) is located in the midbrain and is believed to play a role in reward, pleasure, and addition.

Figure 1C:
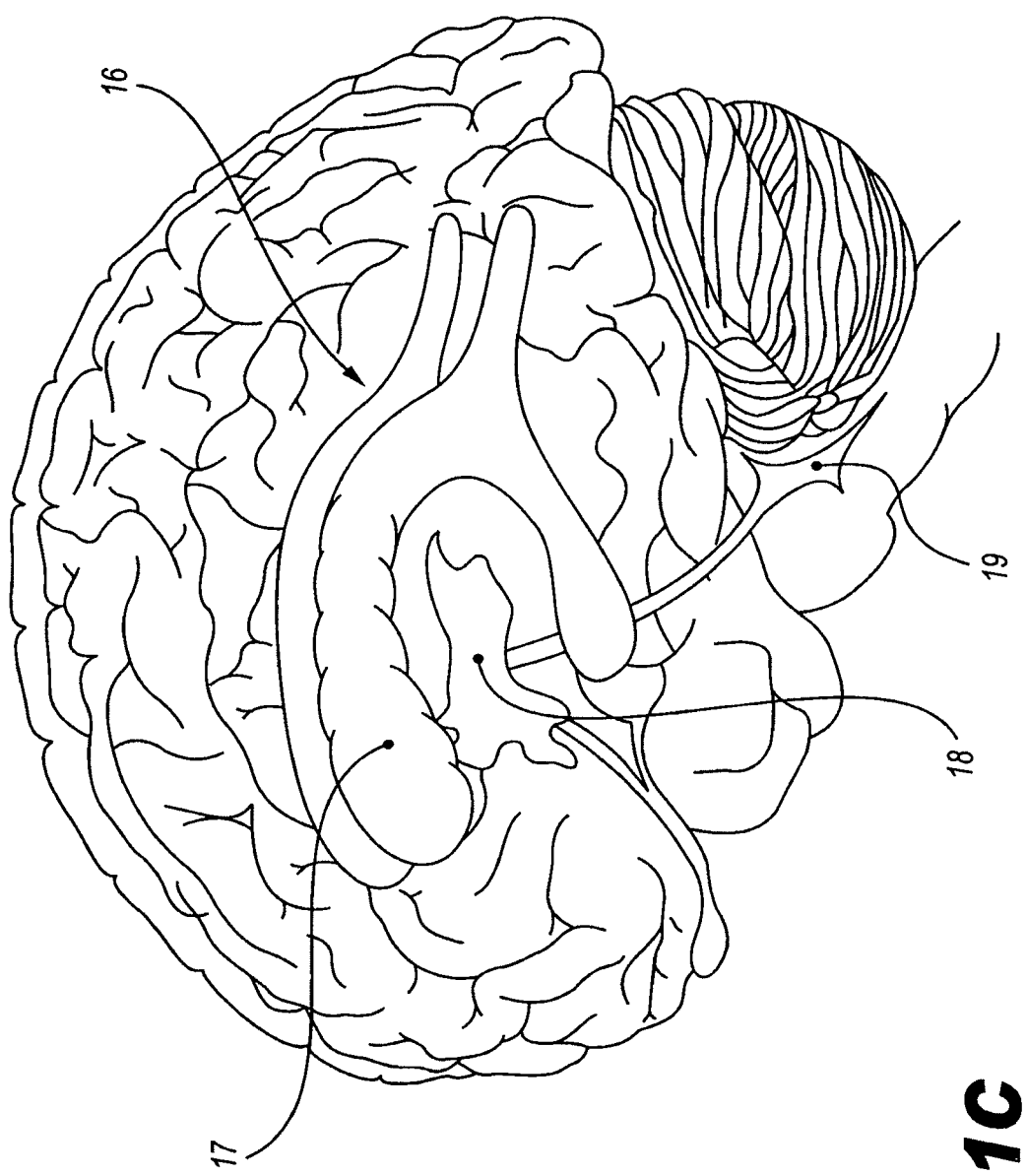
FIG. 1C is another perspective lateral view of the brain and shows the cerebral ventricles.

FIG. 1C is another perspective lateral view of the brain and shows the cerebral ventricles (16). The cerebral ventricles (16) include paired lateral ventricles (17), the third ventricle (18), and the fourth ventricle (19). Each of these cerebral ventricles (16) is filled with cerebrospinal fluid, which is a clear bodily fluid that occupies the subarachnoid space in the brain. The subarachnoid space is the space between the skull and the cerebral cortex (14; FIG. 1A). The cerebrospinal fluid has many functions, one of which is to act as a cushion or buffer for the cerebral cortex (14; FIG. 1A).

Figure 1D:
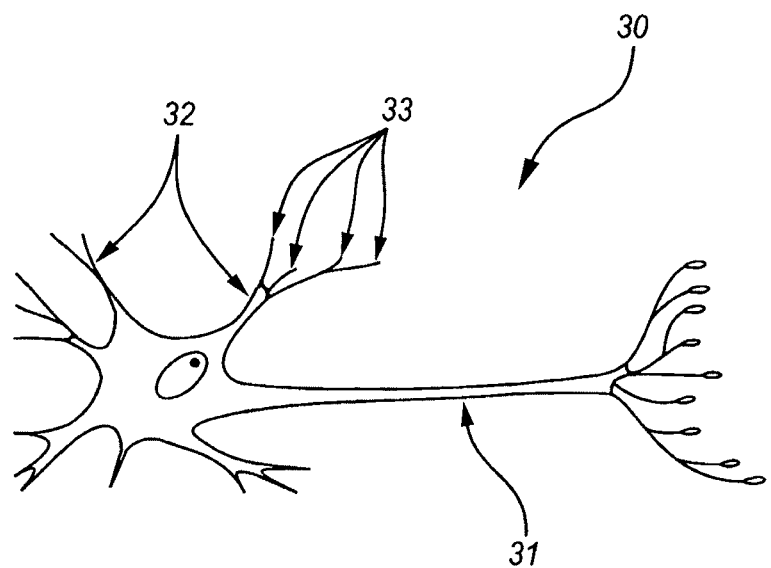
FIG. 1D illustrates an exemplary neuron.

The brain also includes millions of neurons that innervate its various parts. FIG. 1D illustrates an exemplary neuron (30). As shown in FIG. 1D, a neuron (30) includes an axon (31) and a number of dendrites (32). The axon (31) is the long, thread-like part of the nerve cell that extends from the cell body and is configured to transmit nerve impulses to other neurons or to other structures within the patient (e.g., various portions of the brain). Dendrites (32) are the tree-like extensions of the neuron (30), as illustrated in FIG. 1D, and are configured to form synaptic contacts (33) with the terminals of other nerve cells to allow nerve impulses to be transmitted from neuron to neuron.

Synaptic contacts (33), also called synapses, are specialized junctions through which neurons signal to one another and to non-neuronal cells, such as the various areas in the brain as described in connection with FIGS. 1A-1B. Synapses (33) allow neurons to form interconnected neural circuits. Synapses (33) are thus vital to the biological computations that underlie perception and thought. Synapses (33) also allow the nervous system to connect to and control the other systems of the body. Synapses (33) that are no longer used as a person develops are normally removed by the person's nervous system—a process know as neural pruning.

Studies have shown that structures of the frontal lobe, temporal lobe, cingulate gyrus, substantia nigra, thalamus, amygdala, hippocampus, ventral tegmental area, nucleus accumbens, and locus coeruleus exhibit abnormalities in patients with a psychotic disorder or are especially involved in many psychotic disorders. It is believed that applying a stimulus to one or more of these areas within the brain may be useful in treating many psychotic disorders. The stimulus may be used to treat the causes of a psychotic disorder itself and/or any symptom of the disorder.

Consequently, as will be described in more detail below, a stimulator may be implanted in a patient with a psychotic disorder and configured to deliver a stimulus to one or more stimulation sites within the brain to treat the psychotic disorder. As disclosed herein, the stimulation site may include, but is not limited to, one or more of the frontal lobe, temporal lobe, cingulate gyrus, substantia nigra, thalamus, amygdala, hippocampus, ventral tegmental area, nucleus accumbens, and locus coeruleus. The stimulus may include an electrical stimulation current, one or more drugs, gene infusion, chemical stimulation, thermal stimulation, electromagnetic stimulation, mechanical stimulation, and/or any other suitable stimulation.

As used herein, and in the appended claims, the term "stimulator" will be used broadly to refer to any device that delivers a stimulus, such as an electrical stimulation current, one or more drugs or other chemical stimulation, thermal stimulation, electromagnetic stimulation, mechanical stimulation, gene infusion, and/or any other suitable stimulation at a stimulation site to treat a psychotic disorder. Thus, the term "stimulator" includes, but is not limited to, a stimulator, microstimulator, implantable pulse generator (IPG), spinal cord stimulator (SCS), system control unit, cochlear implant, deep brain stimulator, drug pump, or similar device.

Figure 2:
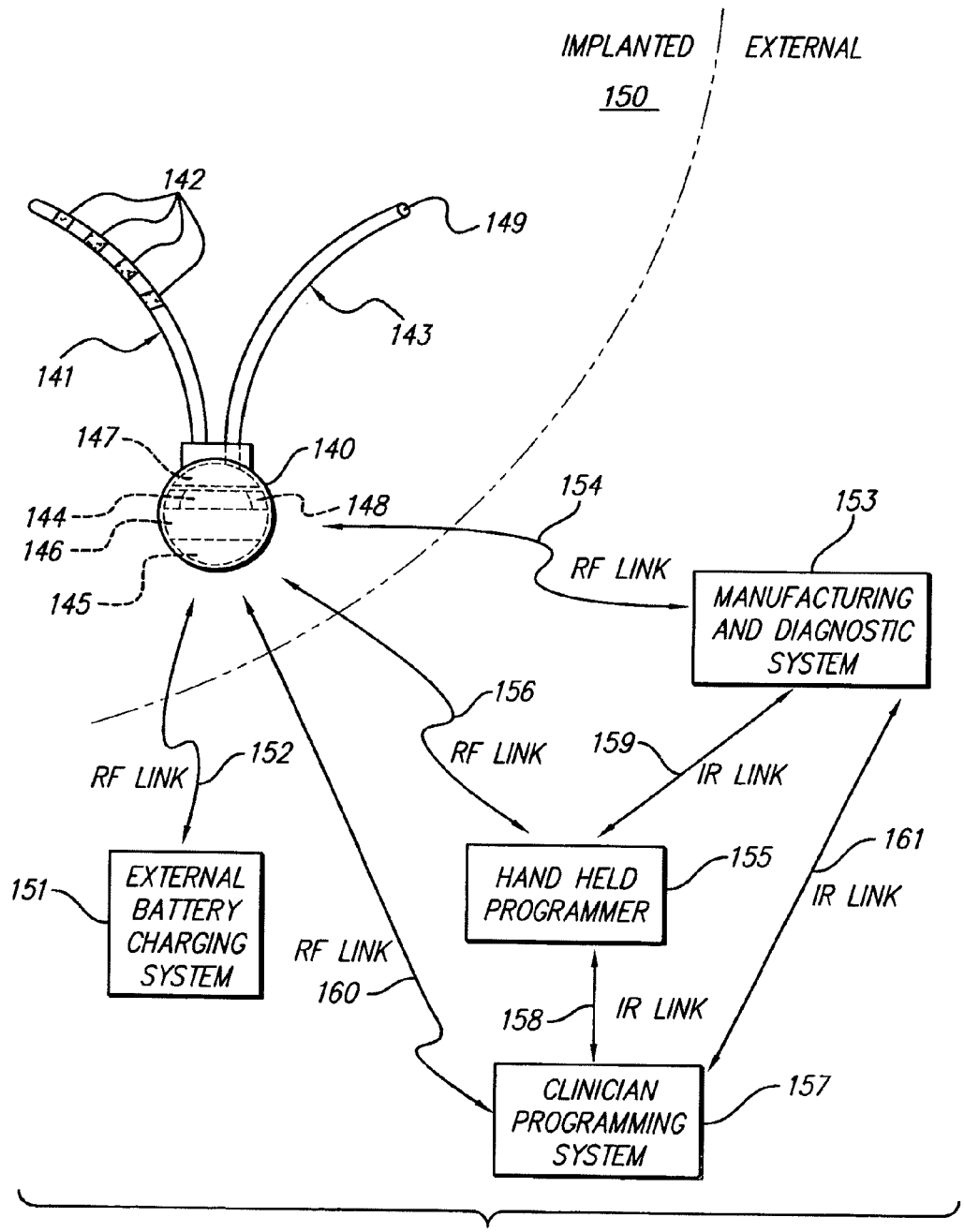
FIG. 2 illustrates an exemplary stimulator that may be used to apply a stimulus to a stimulation site within a patient to treat a psychotic disorder according to principles described herein.

To facilitate an understanding of the methods of optimally treating a psychotic disorder with an implanted stimulator as disclosed herein, a more detailed description of the stimulator and its operation will now be given with reference to the figures. FIG. 2 illustrates an exemplary stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 2 is configured to provide electrical stimulation to a stimulation site within a patient and may include a lead (141) having a proximal end coupled to the body of the stimulator (140). The lead (141) also includes a number of electrodes (142) configured to apply an electrical stimulation current to a stimulation site. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site. In some alternative examples, as will be illustrated in connection with FIG. 3, the stimulator (140) is leadless.

As illustrated in FIG. 2, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171, and U.S. Publications 2001/0046625 A1 and 2001/0053476 A1, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site.

The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus. An exemplary, but not exclusive, intermittent drug infusion rate includes a 24 hour repeating cycle with 8 hours of continuous drug infusion followed by 16 hours of non-infusion. Another example of an intermittent drug infusion rate is a multi-day cycle in which the infusion rate varies each day.

Continuous drug infusion is advantageous with some drugs that are used to treat a psychotic disorder. For example, it is believed that continuous drug infusion of some drugs at various stimulation sites within the patient may effectively treat a psychotic disorder. Conversely, it is believed that some drugs used to treat a psychotic disorder lose efficacy if they are only intermittently infused. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different types, causes, or symptoms of psychotic disorders and/or different patients. Thus, in some embodiments, the stimulation parameters may be adjusted by the patient, a clinician, or other user of the stimulator (140) as best serves the particular patient being treated. The stimulation parameters may also be automatically adjusted by the stimulator (140), as will be described below. For example, the stimulator (140) may increase excitement of a stimulation site by applying a stimulation current having a relatively low frequency (e.g., less than 100 Hz). The stimulator (140) may also decrease excitement of a stimulation site by applying a relatively high frequency (e.g., greater than 100 Hz). The stimulator (140) may also, or alternatively, be programmed to apply the stimulation current to a stimulation site intermittently or continuously.

Additionally, the exemplary stimulator (140) shown in FIG. 2 is configured to provide drug stimulation to a patient with a psychotic disorder by applying one or more drugs at a stimulation site within the patient. The ability to infuse a drug or drugs used to treat a psychotic disorder directly at the stimulation site where the drug acts is very significant. This eliminates the need for the body to pass the drug through the digestive system or blood stream to the stimulation site, which may also prevent unwanted drug side-effects that occur during such transitions. Additionally, in some examples and for similar reasons, local drug infusion with an implantable stimulator (140) allows elevated dosages of drugs to be used without the adverse side effects that accompany typical drug infusion from a device external to the patient.

Hence, to facilitate drug stimulation, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. For example, the pump (147) may include a reservoir configured to hold one or more drugs. In some examples, the volume of the reservoir is sufficiently large so as to contain enough drugs for the patient's anticipated lifetime. Alternatively, the reservoir may be refillable, e.g., through a percutaneous injection with a hypodermic needle.

Controlled drug release devices based upon a mechanical or electromechanical infusion pump may be alternatively used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The one or more drugs that may be applied to a stimulation site to treat a psychotic disorder may have an excitatory effect on the stimulation site. Additionally or alternatively, the one or more drugs may have an inhibitory effect on the stimulation site to treat a psychotic disorder. Exemplary excitatory drugs that may be applied to a stimulation site to treat a psychotic disorder include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat a psychotic disorder include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat a psychotic disorder include at least one or more of the following substances: clozapine, risperidone, olanzapine, quetiapine, ziprasidone, aripiprazole, anesthetic agents, synthetic or natural hormones, neurotransmitters, interleukins, cytokines, lymphokines, chemokines, growth factors, intracellular and intercellular chemical signals and messengers, one or more drugs that block production of β-amyloid, one or more drugs that block aggregation of β-amyloid, one or more drugs that block neuronal toxicity of β-amyloid, chelating agents (e.g., clioquinol), glial line-derived neurotrophic factors (GDNF), immunomodulators (e.g., vaccines targeted against β-amyloid), cholinesterase inhibitors (e.g., Tacrine, Donepezil, Rivastigmine, Galantamine), anti-inflammatory drugs, estrogen replacement drugs, gene therapy agents, neurotrophic factors, antioxidant therapy agents, hormonal therapy agents, and plaque dissolving substances.

Any of the drugs listed above, alone or in combination, or other drugs or combinations of drugs later developed or shown to treat a psychotic disorder or its symptoms may be applied to the stimulation site to treat a psychotic disorder. In some embodiments, the one or more drugs are infused chronically into the stimulation site. Additionally or alternatively, the one or more drugs may be infused acutely into the stimulation site in response to a biological signal or a sensed need for the one or more drugs.

The stimulator (140) of FIG. 2 is illustrative of many types of stimulators that may be used to apply a stimulus to a stimulation site to treat a psychotic disorder. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus at a stimulation site within a patient. Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
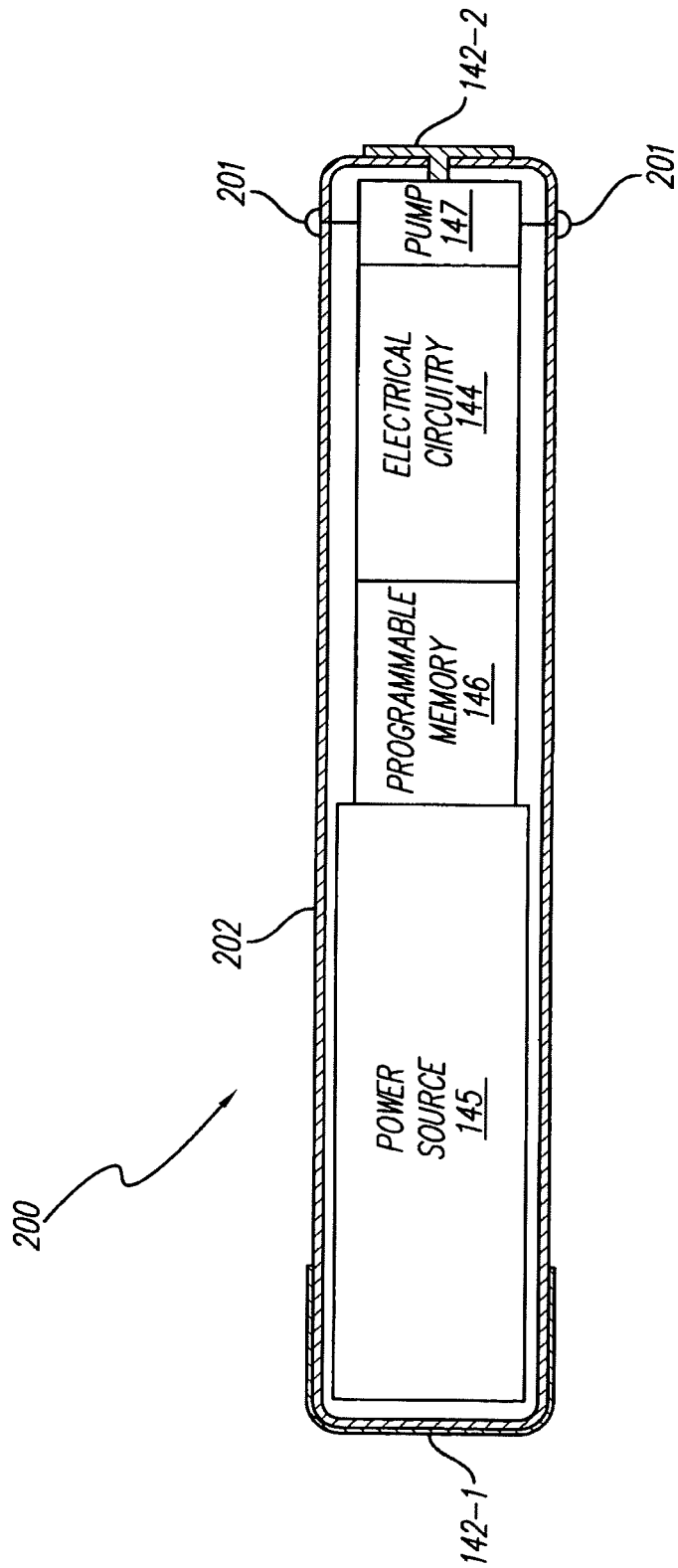
FIG. 3 illustrates an exemplary microstimulator that may be used as the stimulator according to principles described herein.

FIG. 3 illustrates an exemplary microstimulator (200) that may be used as the stimulator (140; FIG. 2) described herein. Other configurations of the microstimulator (200) are possible, as shown in the above-referenced patents and as described further below.

As shown in FIG. 3, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired target nerve, the surrounding area, and the method of implantation. In some embodiments, the volume of the capsule (202) is substantially equal to or less than three cubic centimeters. In some embodiments, the microstimulator (200) may include two or more leadless electrodes (142) disposed on the outer surface of the microstimulator (200).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs at a stimulation site to treat a psychotic disorder. The infusion outlets (201) may dispense one or more drugs directly to the treatment site. Alternatively, catheters may be coupled to the infusion outlets (201) to deliver the drug therapy to a stimulation site some distance from the body of the microstimulator (200). The stimulator (200) of FIG. 3 also includes electrodes (142-1 and 142-2) at either end of the capsule (202). One of the electrodes (142) may be designated as a stimulating electrode to be placed close to the stimulation site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 4:
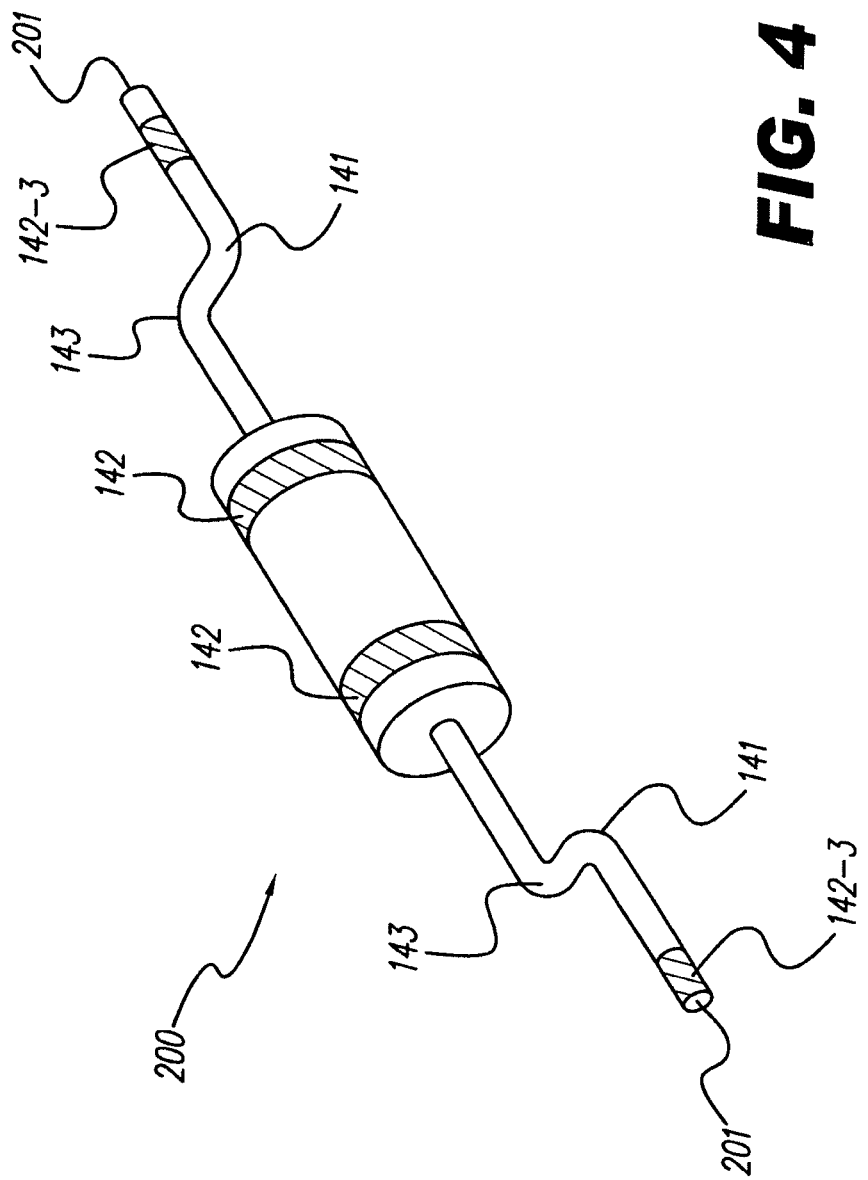
FIG. 4 shows one or more catheters coupled to a microstimulator according to principles described herein.

FIG. 4 shows an example of a microstimulator (200) with one or more catheters (143) coupled to the infusion outlets on the body of the microstimulator (200). With the catheters (143) in place, the infusion outlets (201) that actually deliver the drug therapy to stimulation site are located at the ends of catheters (143). Thus, in the example of FIG. 4, a drug therapy is expelled by the pump (147, FIG. 3) from an infusion outlet (201, FIG. 3) in the casing (202, FIG. 3) of the microstimulator (200), through the catheter (143), out an infusion outlet (201) at the end of the catheter (143) to the stimulation site within the patient. As shown in FIG. 4, the catheters (143) may also serve as leads (141) having one or more electrodes (142-3) disposed thereon. Thus, the catheters (143) and leads (141) of FIG. 4 permit infused drugs and/or electrical stimulation current to be directed to a stimulation site while allowing most elements of the microstimulator (200) to be located in a more surgically convenient site. The example of FIG. 4 may also include leadless electrodes (142) disposed on the housing of the microstimulator (200), in the same manner described above.

Figure 5:
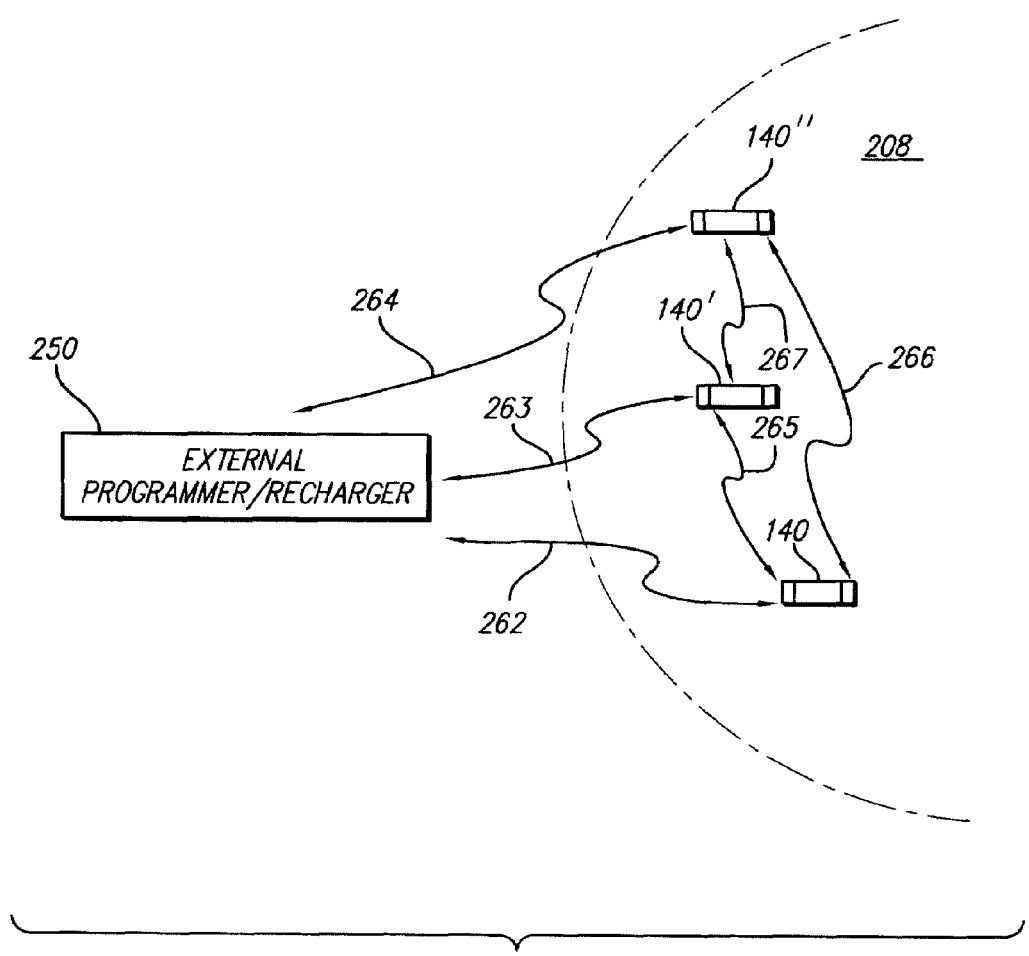
FIG. 5 depicts a number of stimulators configured to communicate with each other and/or with one or more external devices according to principles described herein.

Returning to FIG. 2, the stimulator (140) may be configured to operate independently. Alternatively, as shown in FIG. 5 and described in more detail below, the stimulator (140) may be configured to operate in a coordinated manner with one or more additional stimulators, other implanted devices, or other devices external to the patient's body. For instance, a first stimulator may control, or operate under the control of, a second stimulator, other implanted device, or other device external to the patient's body. The stimulator (140) may be configured to communicate with other implanted stimulators, other implanted devices, or other devices external to the patient's body via an RF link, an ultrasonic link, an optical link, or any other type of communication link. For example, the stimulator (140) may be configured to communicate with an external remote control unit that is capable of sending commands and/or data to the stimulator (140) and that is configured to receive commands and/or data from the stimulator (140).

In order to determine the stimulation parameters required to most effectively treat a psychotic disorder for a particular patient, various indicators of the psychotic disorder and/or the patient's response to treatment may be sensed or measured. These indicators include, but are not limited to, electrical activity of the brain (e.g., EEG); discharge frequency of a neural population in a stimulation site; neurotransmitter levels; hormone levels; dopamine levels; interleukin levels; cytokine levels; lymphokine levels; chemokine levels; growth factor levels; electrolyte levels; enzyme levels; metabolic activity in the brain; blood flow rate in the head, neck or other areas of the body; drug levels within the patient; changes in blood plasma; changes in local interstitial fluid; changes in cerebrospinal fluid; patient or caregiver input, e.g., the stimulation may be in response to a hallucination experienced by a patient; temperature of tissue at the stimulation site; and/or brain hyperexcitability, e.g. increased response of given tissue to the same input. In some embodiments, the stimulator (140) may be configured to adjust the stimulation parameters in a closed loop manner in response to these measurements. The stimulator (140) may be configured to perform the measurements. Alternatively, other sensing devices may be configured to perform the measurements and transmit the measured values to the stimulator (140). Exemplary sensing devices include, but are not limited to, chemical sensors, deep brain sensing leads, electrodes, optical sensors, mechanical (e.g., motion, pressure) sensors, temperature sensors, and Chemically Sensitive Field-Effect Transistors (CHEMFETs) (e.g., Enzyme-Selective Field-Effect Transistors (ENFETs), Ion-Sensitive Field-Effect Transistors).

For instance, one or more stimulators or other recording devices may be used to record neural activity of a stimulation site in order to determine the discharge frequency of the neural population in that stimulation site. The stimulation parameters may then be adjusted in response to the sensed neural activity. For example, the amplitude of the stimulation current may be increased if the discharge frequency is above a programmable threshold frequency (e.g., 50 Hz). The amplitude of the stimulation current may be decreased if the discharge frequency is less than another programmable threshold frequency (e.g., 2 Hz). It will be recognized that the threshold frequencies may vary as best serves a particular application.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of treating a patient with a psychotic disorder may be carried out according to the following sequence of procedures. The steps listed below may be modified, reordered, and/or added to as best serves a particular application.

1. A stimulator (140) is implanted so that its electrodes (142) and/or infusion outlet (149) are in communication with a stimulation site (e.g., the frontal lobe). As used herein and in the appended claims, the term "in communication with" refers to the stimulator (140), stimulating electrodes (142), and/or infusion outlet (149) being adjacent to, in the general vicinity of, in close proximity to, directly next to, or directly on the stimulation site.

2. The stimulator (140) is programmed to apply at least one stimulus to the stimulation site. The stimulus may include electrical stimulation, drug stimulation, gene infusion, chemical stimulation, thermal stimulation, electromagnetic stimulation, mechanical stimulation, and/or any other suitable stimulation.

3. When the patient or clinician desires to invoke stimulation, the patient sends a command to the stimulator (140) (e.g., via a remote control) such that the stimulator (140) delivers the prescribed stimulation. The stimulator (140) may be alternatively or additionally configured to automatically apply the stimulation in response to sensed indicators of a psychotic disorder.

4. To cease stimulation, the stimulator (140) may be turned off (e.g., via a remote control).

5. Periodically, the power source (145) of the stimulator (140) is recharged, if necessary, in accordance with Function 1 described above. As will be described below, this recharging function can be made much more efficient using the principles disclosed herein.

In other examples, the treatment administered by the stimulator (140), i.e., drug therapy and/or electrical stimulation, may be automatic and not controlled or invoked by the patient.

For the treatment of different patients, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to stimulate multiple stimulation sites (e.g., the cerebral cortex and the hippocampus.

As shown in the example of FIG. 5, a first stimulator (140) implanted beneath the skin of the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. stimulator (140), may control, or operate under the control of, another implanted device(s), e.g. stimulator (140') and/or stimulator (140"). Control lines (262-267) have been drawn in FIG. 5 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 5 may be configured to sense various indicators of a psychotic disorder and transmit the measured information to the third stimulator (140"). The third stimulator (140") may then use the measured information to adjust its stimulation parameters and apply stimulation to a stimulation site accordingly. The various implanted stimulators may, in any combination, sense indicators of the psychotic disorder, communicate or receive data on such indicators, and adjust stimulation parameters accordingly.

Alternatively, the external device (250) or other external devices communicating with the external device may be configured to sense various indicators of a patient's condition. The sensed indicators can then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

The stimulator (140) of FIG. 2 may be implanted within a patient using any suitable surgical procedure such as, but not limited to, injection, small incision, open placement, laparoscopy, or endoscopy. Exemplary methods of implanting a microstimulator, for example, are described in U.S. Pat. Nos. 5,193,539; 5,193,540; 5,312,439; 6,185,452; 6,164,284; 6,208,894; and 6,051,017. Exemplary methods of implanting an SCS, for example, are described in U.S. Pat. Nos. 5,501, 703; 6,487,446; and 6,516,227. Exemplary methods of implanting a deep brain stimulator, for example, are described in U.S. Pat. Nos. 5,938,688; 6,016,449; and 6,539, 263. All of these listed patents are incorporated herein by reference in their respective entireties.

Figure 6:
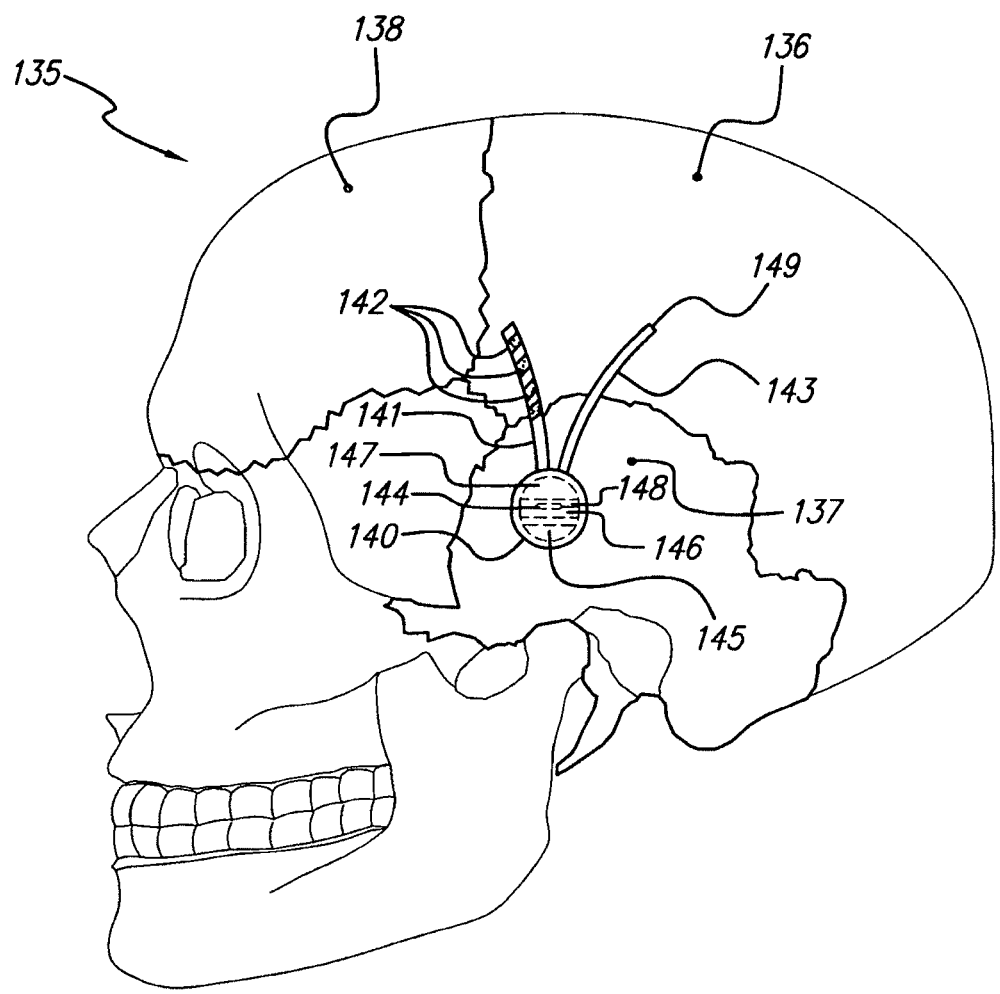
FIG. 6 illustrates a stimulator that has been implanted beneath the scalp of a patient to stimulate a stimulation site within the brain associated with a psychotic disorder according to principles described herein.

By way of example, FIG. 6 shows a stimulator (140) (e.g., a deep brain stimulator) that has been implanted beneath the scalp of a patient to stimulate a stimulation site within the brain associated with a psychotic disorder. The stimulator (140) may be implanted in a surgically-created shallow depression or opening in the skull (135). For instance, the depression may be made in the parietal bone (136), temporal bone (137), frontal bone (138), or any other bone within the skull (135) as best serves a particular application. The stimulator (140) may conform to the profile of surrounding tissue (s) and/or bone(s), thereby minimizing the pressure applied to the skin or scalp. Additionally or alternatively, the stimulator (140) may be implanted in a subdural space over any of the lobes of the brain or in a cerebral ventricle.

In some embodiments, as shown in FIG. 6, a lead (141) and/or catheter (143) run subcutaneously to an opening in the skull (135) and pass through the opening such that it is in communication with a stimulation site in the brain. Alternatively, the stimulator (140) is leadless and is configured to generate a stimulus that passes through the skull. In this manner, the brain may be stimulated without having to physically invade the brain itself.

Figure 7:
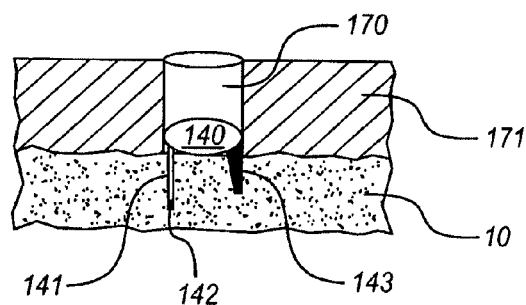
FIG. 7 is cross-sectional view of a stimulator implanted within a hole created in the skull of a patient with a psychotic disorder according to principles described herein.

Alternatively, as shown in the cross-sectional view of FIG. 7, the stimulator (140) may be implanted within the lumen of a hole (170) created in the skull (171) and configured to apply a stimulus to a stimulation site within the brain (e.g., the frontal lobe (10)). The hole (170) may be a burr hole, for example, and may be created with a surgical drill or any other suitable device. The hole (170) extends at least partially into the skull (171), and, as shown in FIG. 7, may extend all the way through the skull (171). The stimulator (140) is placed within the lumen of the hole (170) and coupled to the walls of the hole (170) and/or the top surface of the stimulation site, e.g., the frontal lobe (10), using an adhesive, suture, or any other fastening device. Once the stimulator (140) has been implanted, the hole (170) may be covered by an appropriately sized cap (not shown).

As shown in FIG. 7, a lead (141) may be coupled to the stimulator (140) with the distal end of the lead (141) being routed to a particular location within the frontal lobe (10) or other stimulation site in the brain. The distal end of the lead (141) may include one or more electrodes (142) configured to deliver an electrical stimulation current to the stimulation site. A catheter (143) may additionally or alternatively be coupled to the stimulator (140) and routed to the stimulation site so as to deliver one or more drugs at the stimulation site.

Figure 8A:
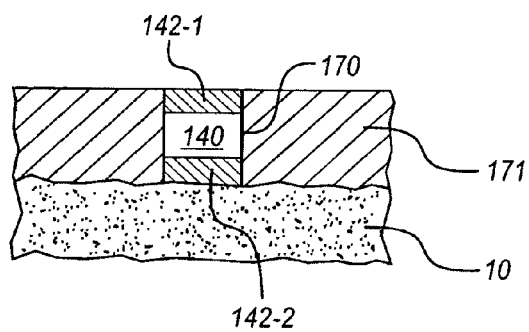
FIG. 8A is a cross-sectional view of a stimulator having two ring-like electrodes disposed on its surface implanted within a hole created in the skull of a patient with a psychotic disorder according to principles described herein.
Figure 8B:
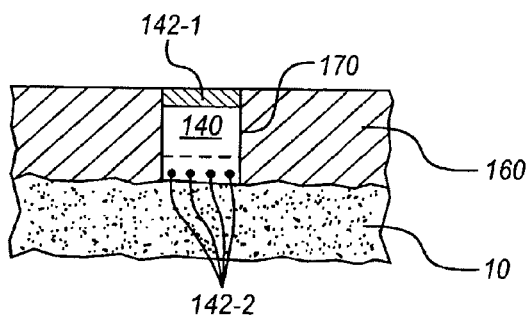
FIG. 8B is a cross-sectional view of a stimulator having multiple electrodes disposed thereon implanted within a hole created in the skull of a patient with a psychotic disorder according to principles described herein.

As mentioned, the stimulator (140) may be leadless. FIGS. 8A-8B are cross sectional views of exemplary leadless stimulators (140) that have been implanted within the lumen of a hole (170) created in the skull (171). In this manner, the stimulation site within the brain may be stimulated without having to physically invade the brain itself.

For example, FIG. 8A shows an exemplary stimulator (140) with two ring-like electrodes (142) disposed on its surface. The electrode (142-2) more proximal to the stimulation site, e.g., the frontal lobe (10), may be configured to act as a stimulating electrode while the electrode (142-2) more distal to the stimulation site may be configured to act as the indifferent electrode.

FIG. 8B shows an alternative electrode arrangement wherein the end most proximal to the stimulation site includes multiple electrodes (142-2) disposed thereon. Each electrode (142-2) may be selectively configured to act as either an anode or cathode so that monopolar and/or multipolar stimulation may be applied to the stimulation site. The distal end of the stimulator (140) may also include a selectively programmable electrode (142).

Figure 9:
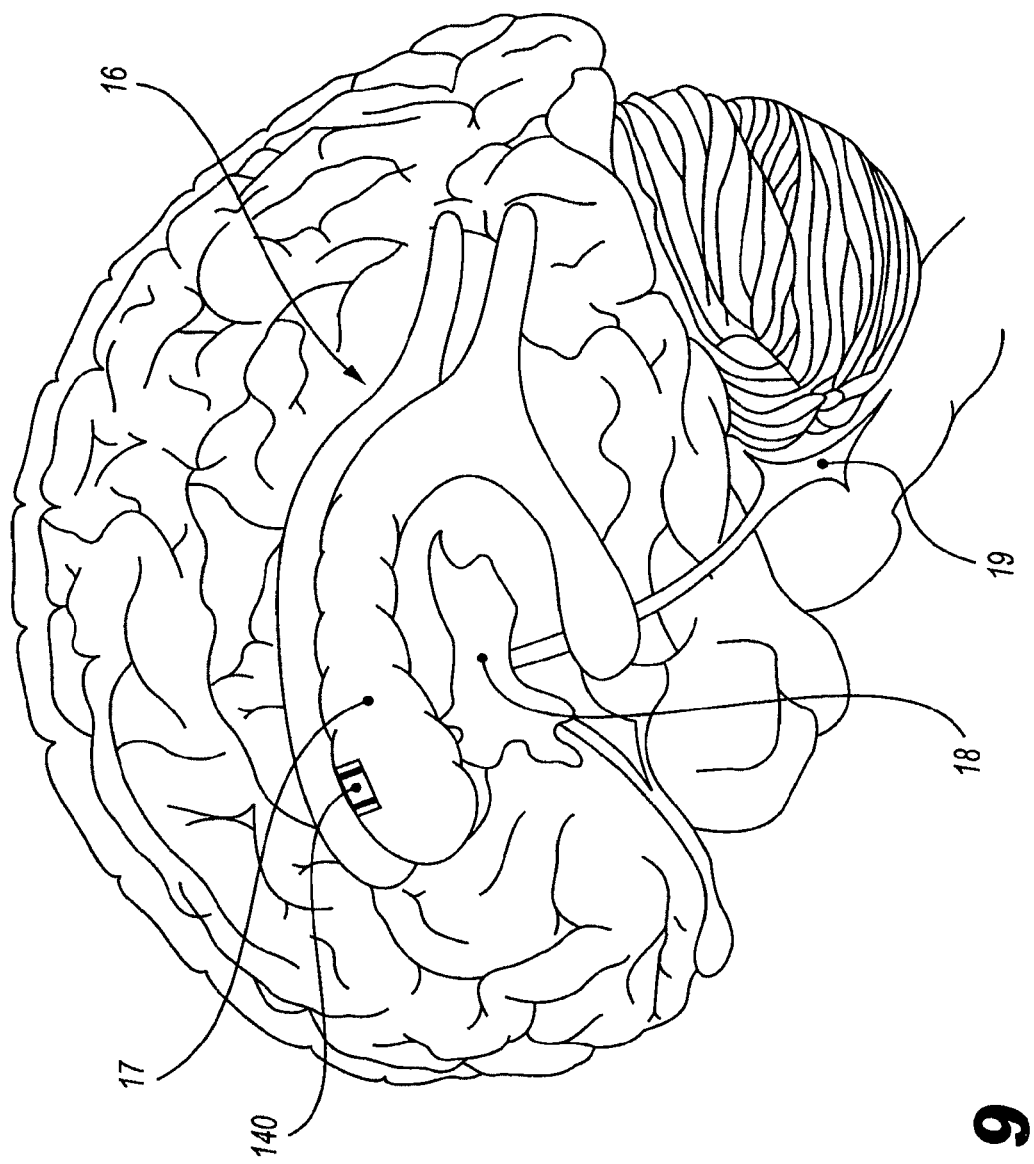
FIG. 9 illustrates an exemplary stimulator that has been implanted within the lateral ventricle according to principles described herein.

In some examples, a psychotic disorder is treated by applying the stimulus to the cerebrospinal fluid found within the cerebral ventricles. To this end, the stimulator (140), stimulating lead (141), and/or catheter (143) may be implanted within one of the cerebral ventricles. For example, FIG. 9 illustrates an exemplary stimulator (140) that has been implanted within the lateral ventricle (17). The stimulator (140) may be coupled to one of the walls of the lateral ventricle (17) using any suitable fixation device (e.g., sutures, adhesives, hooks, or barbs). Alternatively, the stimulator (140) is implanted in a more distal location (e.g., within the nasal epithelium or chest) and coupled to a lead and/or catheter that extends into one of the cerebral ventricles.

The stimulation provided by the stimulator (140) may be configured to treat a psychotic disorder in a number of different ways. For example, in patients suffering from a psychotic disorder, the stimulation may be configured to decrease the activity of one or more stimulation sites that chronically exhibit abnormally increased activity relative to control subjects. The stimulation may alternatively be configured to increase the activity of one or more stimulation sites that chronically exhibit abnormally decreased activity relative to control subjects. The stimulation may additionally or alternatively be configured to break up regions of dense plaque concentration, prevent neural degeneration, promote neural pruning and/or regenerate damaged neurons and synaptic connections to treat the psychotic disorder.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a psychotic disorder comprising at least one of schizophrenia, a delusional disorder, a schizoaffective disorder, said method comprising:
    applying at least one stimulus to a stimulation site within a patient with an implanted stimulator in accordance with one or more stimulation parameters to treat said psychotic disorder; and
    sensing at least one indicator related to said psychotic disorder and using said at least one sensed indicator to adjust one or more of said stimulation parameters;
    wherein said stimulation site comprises at least one or more of a frontal lobe, temporal lobe, cingulate gyrus, substantia nigra, thalamus, amygdala, hippocampus, ventral tegmental area, nucleus accumbens, and locus coeruleus; and
    wherein said at least one indicator comprises a change in cerebrospinal fluid.

2. The method of claim 1, wherein applying the at least one stimulus to the stimulation site within the patient with the implanted stimulator comprises delivering a stimulation current via one or more electrodes coupled to the implanted stimulator.

3. The method of claim 1, wherein applying the at least one stimulus to the stimulation site within the patient with the implanted stimulator comprises a decreased activity of said stimulation site to treat said psychotic disorder.

4. The method of claim 1, wherein applying the at least one stimulus to the stimulation site within the patient with the implanted stimulator comprises an increased activity of said stimulation site to treat said psychotic disorder.

5. The method of claim 1, wherein the stimulus comprises at least one of an electrical stimulation, a drug stimulation, a gene infusion, a chemical stimulation, a thermal stimulation, an electromagnetic stimulation, and a mechanical stimulation.

6. The method of claim 1, further comprising implanting the implanted stimulator at the stimulation site.

7. The method of claim 6, wherein applying the at least one stimulus to the stimulation site within the patient with the implanted stimulator comprises delivering a stimulation current via one or more electrodes coupled to the implanted stimulator, and implanting the implanted stimulator comprises implanting the one or more electrodes in communication with the stimulation site.

8. A method of treating a psychotic disorder comprising at least one of schizophrenia, a delusional disorder, a schizoaffective disorder, said method comprising:
    applying at least one stimulus to a stimulation site within a patient with an implanted stimulator in accordance with one or more stimulation parameters to treat said psychotic disorder; and
    sensing at least one indicator related to said psychotic disorder and using said at least one sensed indicator to adjust one or more of said stimulation parameters;
    wherein said stimulation site comprises at least one or more of a frontal lobe, temporal lobe, cingulate gyrus, substantia nigra, thalamus, amygdala, hippocampus, ventral tegmental area, nucleus accumbens, and locus coeruleus; and wherein said at least one indicator comprises at least one of an interleukin level, a cytokine level, a lymphokine level, a chemokine level, a growth factor level, an electrolyte level, and an enzyme level.

9. The method of claim 8, wherein applying the at least one stimulus to the stimulation site within the patient with the implanted stimulator comprises delivering a stimulation current via one or more electrodes coupled to the implanted stimulator, and further comprising implanting the one or more electrodes in communication with the stimulation site.

10. The method of claim 8, further comprising implanting the implanted stimulator at the stimulation site.

11. The method of claim 8, wherein said stimulus comprises one or more drugs delivered to said stimulation site.

12. The method of claim 8, wherein said stimulus comprises a stimulation current delivered to said stimulation site and one or more drugs delivered to said stimulation site.

* * * * *